United States Patent
Koudymov et al.

(10) Patent No.: US 8,277,734 B2
(45) Date of Patent: Oct. 2, 2012

(54) BIOLOGICAL ACTIVITY MONITORING AND/OR SUPPRESSION

(75) Inventors: Alexei Koudymov, Troy, NY (US);
Michael Shur, Latham, NY (US);
Remigijus Gaska, Columbia, SC (US)

(73) Assignee: Sensor Electronic Technology, Inc., Columbia, SC (US)

( * ) Notice: Subject to any disclaimer, the term of this patent is extended or adjusted under 35 U.S.C. 154(b) by 431 days.

(21) Appl. No.: 12/464,413

(22) Filed: May 12, 2009

(65) Prior Publication Data
US 2009/0280035 A1 Nov. 12, 2009

Related U.S. Application Data

(60) Provisional application No. 61/127,339, filed on May 12, 2008.

(51) Int. Cl.
*A61L 2/28* (2006.01)
*A61L 2/24* (2006.01)
*A61L 2/00* (2006.01)
*G01D 11/26* (2006.01)
*G01N 1/00* (2006.01)
*G01N 33/02* (2006.01)
*G01N 21/00* (2006.01)
*G01N 21/75* (2006.01)
*F01N 3/20* (2006.01)
*G05B 1/00* (2006.01)
*B01J 19/00* (2006.01)
*F24F 3/16* (2006.01)

(52) U.S. Cl. ............ 422/119; 422/105; 422/108; 422/3; 422/22; 436/20; 436/164; 62/78; 62/126

(58) Field of Classification Search .................. 422/119, 422/22; 62/78, 126; 436/20
See application file for complete search history.

(56) References Cited

U.S. PATENT DOCUMENTS

| 4,909,040 | A | * | 3/1990 | Feltrin | 62/78 |
| 5,901,564 | A | | 5/1999 | Comeau, II | |
| 5,946,919 | A | * | 9/1999 | McKinney et al. | 62/3.7 |
| 6,477,853 | B1 | | 11/2002 | Khorram | |
| 7,296,422 | B2 | | 11/2007 | Strohm et al. | |
| 2003/0132398 | A1 | * | 7/2003 | Wang | 250/492.1 |
| 2005/0254055 | A1 | * | 11/2005 | Peng | 356/432 |
| 2006/0019331 | A1 | * | 1/2006 | Eden | 435/34 |
| 2006/0130498 | A1 | * | 6/2006 | Joshi et al. | 62/127 |
| 2008/0138841 | A1 | * | 6/2008 | Vegvary et al. | 435/7.32 |

FOREIGN PATENT DOCUMENTS
WO WO 2006089362 A1 * 8/2006

OTHER PUBLICATIONS

O. Bilenko et al; "Water Disinfection Using Semiconductor Deep Ultraviolet Lighting-Emitting Diodes", MRS 2007 Fall Meeting Abstracts, 1 page.

* cited by examiner

*Primary Examiner* — Jill Warden
*Assistant Examiner* — Charles D Hammond
(74) *Attorney, Agent, or Firm* — Hoffman Warnick LLC

(57) ABSTRACT

Ultraviolet radiation is shone within an area and detected. The detected ultraviolet radiation is monitored over a period of time to determine a set of biological activity dynamics for the area. Ultraviolet radiation detected during a calibration period can be used to provide a baseline with which analysis of subsequently detected ultraviolet radiation is compared and analyzed. When the presence of biological activity is determined within the area, ultraviolet radiation and/or one or more other approaches can be utilized to suppress the biological activity.

21 Claims, 4 Drawing Sheets

BIOLOGICAL ACTIVITY MONITORING AND/OR SUPPRESSION

REFERENCE TO PRIOR APPLICATION

The current application claims the benefit of co-pending U.S. Provisional Application No. 61/127,339, titled "Active bacteria control system", which was filed on 12 May 2008, and which is hereby incorporated by reference.

TECHNICAL FIELD

The disclosure relates generally to biological activity, such as bacterial growth, monitoring and/or suppression, and more particularly, to a solution for monitoring and/or suppressing biological activity within an area, such as a storage area of a refrigerated unit, using ultraviolet radiation.

BACKGROUND ART

Reliable, hygienic storage of items, such as food, is a major problem. For example, the problem is present throughout the food industry, e.g., manufacturers, retailers, restaurants, and in every household, and is especially significant for food service establishments, in which related issues of food quality control are also significant. In addition to food storage and quality control in fixed locations (e.g., a refrigerator) where access to electricity is readily available, proper food storage and quality control is also important in situations, such as picnics, camping, mobile food kiosks, hospitality or battlefield meal locations, search and rescue, etc., for which access to unlimited electricity and/or a stationary storage device, such as a refrigerator, is not available. In addition to food storage, other items also require hygienic storage. For example, medical and chemical equipment, construction wood, etc., also require storage in a biologically safe environment. Since ambient temperature significantly affects bacterial activity, effective control of the ambient temperature is an important tool in ensuring reliable, hygienic storage of various items.

In the food industry, bacteria, including those responsible for food-borne illness, often cannot be readily seen. Bacteria responsible for food-borne illness, such as *Campylobacter jejuni*, *Clostridium botulinum*, *Clostridium perfringens*, *Escherichia coli* O157:H7, *Salmonella*, *Streptococcus* A, *Listeria* monocytogenes, *Shigella*, *Staphylococcus aureus*, etc., can be present in food at the time of purchase or seeded during storage, particularly when packaging is opened or damaged. Such bacteria can be especially dangerous if present on food that is consumed without sufficient thermal treatment to kill the bacteria. Too often, humans and other animals suffer illness from the effects of undetected bacteria in food that was consumed. Other bacteria, which does not cause health problems, can affect the quality and taste of the food when present.

It has long been shown that ultraviolet radiation interacts with biologically active media. In particular, an absorption spectrum of a DNA molecule has a peak wavelength at about 265 nanometers, which is within the ultraviolet-C electromagnetic spectrum range of 100 to 280 nanometers. RNA and proteins also have absorption peaks in the ultraviolet-C electromagnetic spectrum range, from 215 to 280 nm. Therefore, the absorption of electromagnetic radiation within the UV-C range, and especially near 265 nanometers, as well as the photoluminescence in response to such radiation, is typically an indicator of biological activity, such as bacterial activity. Additionally, the more ultraviolet radiation that is absorbed by bacteria DNA, the more DNA molecules are destroyed, thereby preventing the reproduction process. As a result, ultraviolet radiation can be used to control bacterial growth.

However, detection of the presence of bacteria is often not sufficient to make a decision regarding spoilage or a condition of a stored item, such as food or a chemical. In particular, an intensity of a response to ultraviolet radiation strongly depends on the particular bacteria type(s), concentration(s), and location(s). Additionally, a similar fluorescent signal can be generated by certain food species, thereby providing a false indication of the presence of bacteria.

SUMMARY OF THE INVENTION

The inventors provide a solution for monitoring and/or suppressing (e.g., controlling and/or preventing) biological activity, such as bacteria multiplication, while an item is being stored in a manner that does not affect desirable attributes of the stored item. For example, an embodiment of the solution is configured to monitor and suppress bacteria multiplication while food is stored within a refrigerator without affecting the quality of the food. Similarly, biological activity that may occur within the storage environment of other items, such as medical and chemical equipment, construction wood, and/or the like, can be monitored, controlled, and/or prevented.

Aspects of the invention provide a solution in which ultraviolet radiation is shone within an area and detected. The detected ultraviolet radiation is monitored over a period of time to determine a set of biological activity dynamics for the area. Ultraviolet radiation detected during a calibration period can be used to provide a baseline with which analysis of subsequently detected ultraviolet radiation is compared and analyzed. When the presence of biological activity is determined within the area, ultraviolet radiation and/or one or more other approaches can be utilized to suppress the biological activity.

A first aspect of the invention provides a system comprising: an ultraviolet radiation source configured to generate ultraviolet radiation shone within an area; an ultraviolet radiation detector configured to sense ultraviolet radiation within the area; and a component configured to monitor the ultraviolet radiation sensed by the ultraviolet radiation detector over a period of time and to determine a set of biological activity dynamics for the area based on the sensed ultraviolet radiation and the period of time.

A second aspect of the invention provides a storage device comprising: a storage area configured to store at least one item; an ultraviolet radiation source configured to generate ultraviolet radiation shone within the storage area; an ultraviolet radiation detector configured to sense ultraviolet radiation within the storage area; and a component configured to monitor the ultraviolet radiation sensed by the ultraviolet radiation detector over a period of time and to determine a set of biological activity dynamics for the storage area based on the monitored ultraviolet radiation and the period of time.

A third aspect of the invention provides a refrigeration device comprising: a storage area configured to store at least one refrigerated item; a component configured to control at least one environmental condition of the storage area, wherein the at least one environmental condition includes at least one of: a temperature, a humidity, a gas convection, or a fluid convection; an ultraviolet radiation source configured to generate ultraviolet radiation shone within the storage area; an ultraviolet radiation detector configured to sense ultraviolet radiation within the storage area; and a component configured to monitor the ultraviolet radiation sensed by the ultraviolet radiation detector over a period of time and to determine a set of biological activity dynamics for the storage area based on the monitored ultraviolet radiation and the period of time.

The illustrative aspects of the invention are designed to solve one or more of the problems herein described and/or one or more other problems not discussed.

BRIEF DESCRIPTION OF THE DRAWINGS

These and other features of the disclosure will be more readily understood from the following detailed description of the various aspects of the invention taken in conjunction with the accompanying drawings that depict various aspects of the invention.

It is noted that the drawings may not be to scale. The drawings are intended to depict only typical aspects of the invention, and therefore should not be considered as limiting the scope of the invention. In the drawings, like numbering represents like elements between the drawings.

DETAILED DESCRIPTION OF THE INVENTION

As indicated above, aspects of the invention provide a solution in which ultraviolet radiation is shone within an area and detected. The detected ultraviolet radiation is monitored over a period of time to determine a set of biological activity dynamics for the area. Ultraviolet radiation detected during a calibration period can be used to provide a baseline with which analysis of subsequently detected ultraviolet radiation is compared and analyzed. When the presence of biological activity is determined within the area, ultraviolet radiation and/or one or more other approaches can be utilized to suppress the biological activity. As used herein, unless otherwise noted, the term "set" means one or more (i.e., at least one) and the phrase "any solution" means any now known or later developed solution. Further, as used herein, ultraviolet radiation/light means electromagnetic radiation having a wavelength ranging from approximately 10-400 nanometers, while ultraviolet-C (UV-C) means electromagnetic radiation having a wavelength ranging from approximately 100-280 nanometers.

Figure 1:
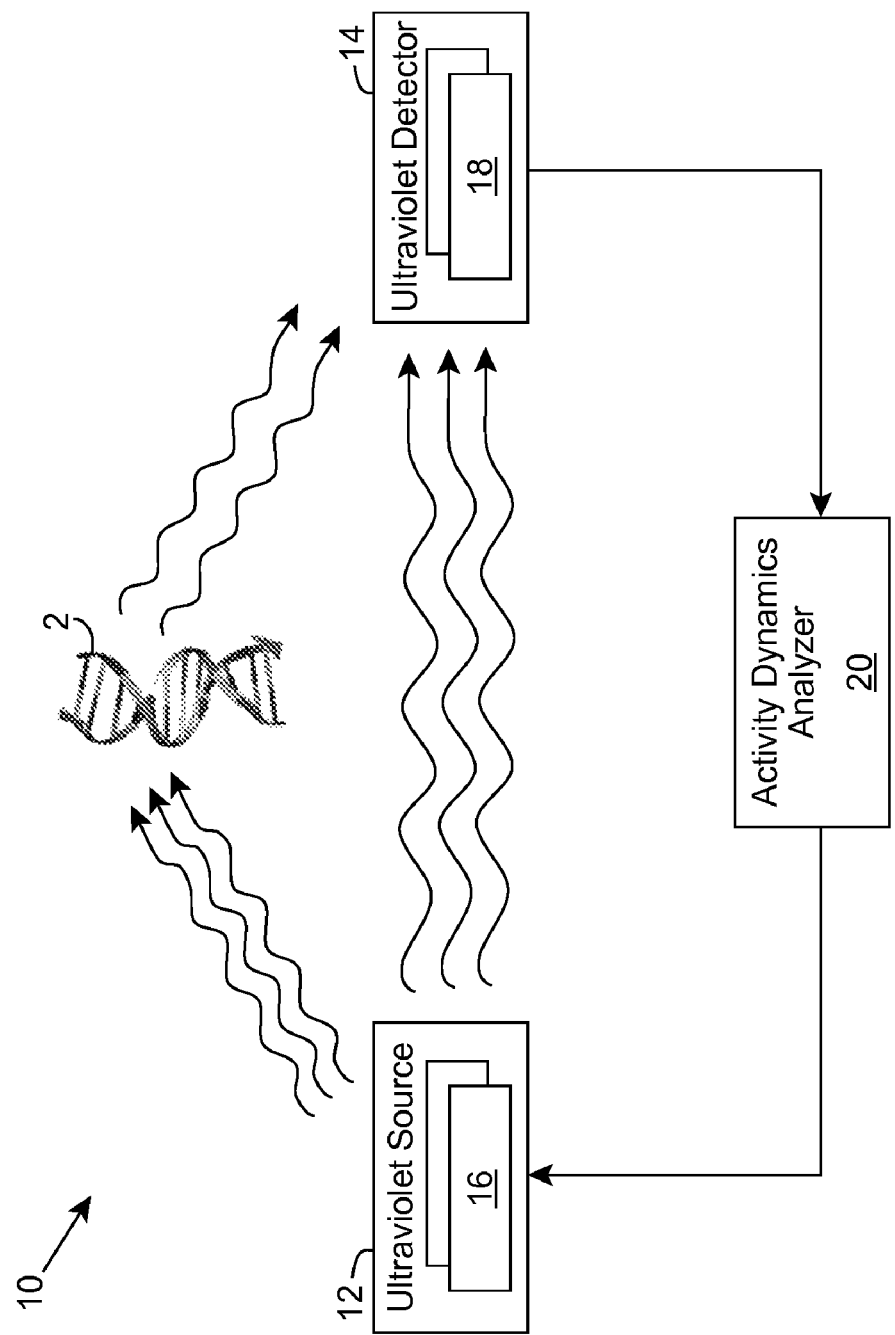
FIG. 1 illustrates the principle of determining a set of biological activity dynamics according to an embodiment.

Turning to the drawings, FIG. 1 illustrates the principle of determining a set of biological activity dynamics according to an embodiment. For example, bacteria population dynamics can be described by three phases: latent; exponential growth; and stationary. During the latent phase, a bacteria population is low and grows slowly while the bacteria synthesizes ribosomal RNA and subsequent enzymes. During exponential growth, the bacteria population undergoes its maximum rate of reproduction, such that the number of bacteria increases directly with time, yielding a straight slope in a logarithmic scale. Using an *E. coli* bacteria population as an example, the exponential growth phase lasts for approximately twenty minutes. During the stationary phase, the bacteria population stabilizes and waste poisons are accumulated in the environment.

The set of biological activity dynamics can include one or more attributes of biological activity that is determined to be occurring within a monitored area. For example, the set of biological activity dynamics can include a presence of biological activity (e.g., exponential bacterial growth), a location of the biological activity, a type of biological activity (e.g., type of organism), a concentration of the biological activity, an estimated amount of time an organism has been in a growth phase (e.g., exponential growth and/or stationary), and/or the like. The set of biological activity dynamics can include information on the variation of the biological activity over time, such as a growth rate, a rate with which an area including the biological activity is spreading, and/or the like. In an embodiment, the set of biological activity dynamics are related to various attributes of bacteria activity within an area, including, for example, the presence of detectable bacteria activity, measured bacteria population/concentration time dynamics, growth phase, and/or the like.

As illustrated, a system 10 can include an ultraviolet source component 12 configured to generate ultraviolet radiation, an ultraviolet detector component 14 configured to sense ultraviolet radiation, and an activity dynamics analyzer 20 configured to operate components 12, 14, and process data received from ultraviolet detector component 14. Ultraviolet source component 12 can comprise any combination of one or more ultraviolet radiation emitters 16. Each ultraviolet radiation emitter 16 can comprise a narrow band or monochromatic ultraviolet light emitter or a broad band ultraviolet light emitter. A particular spectral power distribution for the wavelength/range of wavelengths generated by an ultraviolet radiation emitter 16 can be selected using any solution. For example, an ultraviolet radiation emitter 16 can comprise: an ultraviolet light emitting diode, an ultraviolet light emitting laser, a mercury lamp, and/or the like. In an embodiment, ultraviolet source component 12 includes a set of light emitting diodes 16 manufactured with one or more layers of materials selected from the group-III nitride material system (e.g., $Al_XIn_YGa_{1-X-Y}N$, where $0 \leq X, Y \leq 1$, and $X+Y \leq 1$ and/or alloys thereof). Additionally, ultraviolet source component 12 can comprise one or more additional components (e.g., a wave guiding structure, system for relocating and/or redirecting ultraviolet source(s), etc.) to direct and/or deliver the emitted radiation to a particular location/area, in a particular direction, in a particular pattern, and/or the like. Illustrative wave guiding structures include, but are not limited to, a plurality of ultraviolet fibers, each of which terminates at an opening, a diffuser, and/or the like.

Similarly, ultraviolet detector component 14 can comprise any combination of one or more ultraviolet radiation detectors 18. Each ultraviolet radiation detector 18 can comprise any type of ultraviolet radiation detector, such as a solid state ultraviolet radiation detector manufactured with one or more layers of materials selected from the group-III nitride material system (e.g., $Al_XIn_YGa_{1-X-Y}N$, where $0 \leq X, Y \leq 1$, and $X+Y \leq 1$ and/or alloys thereof). For example, an ultraviolet radiation detector 18 can comprise any type of ultraviolet sensing device, such as an ultraviolet-sensitive photodetector (e.g., an ultraviolet photodiode). In an embodiment, an ultraviolet radiation detector 18 can be selected based on its sensitivity to a particular, narrow band of ultraviolet light, which can be selected using any solution. Additionally, ultraviolet detector component 14 can comprise one or more additional components (e.g., a wave guiding structure, filter, system for moving and/or redirecting ultraviolet detector(s), etc.) to detect ultraviolet radiation in a particular location/direction using an ultraviolet radiation detector 18, make ultraviolet radiation detector 18 sensitive to a particular range of wavelengths, and/or the like.

As discussed herein, ultraviolet radiation interacts with biologically active media. For example, a DNA molecule 2 has a peak absorption spectrum of ultraviolet radiation having a wavelength of approximately 265 nanometers, while RNA and proteins have peak absorption spectrums in the range of 215 to 280 nanometers. To this extent, the presence of DNA 2, RNA, and/or proteins in an area illuminated by an ultraviolet source component 12 can alter an amount of the ultraviolet radiation that is detected by ultraviolet detector component 14. In an embodiment, ultraviolet source component 12 includes emitter(s) 16 that generate ultraviolet light having a wavelength within the UV-C range, and more particularly a wavelength of approximately 265 nanometers (e.g., 250 to 280 nanometers), and ultraviolet detector component 14 includes detector(s) sensitive to ultraviolet light within the UV-C range, and more particularly having a wavelength of approximately 265 nanometers (e.g., 250 to 280 nanometers).

In an embodiment, activity dynamics analyzer 20 analyzes an amount of ultraviolet radiation detected by ultraviolet detector component 14 over time to monitor biological activity in an area. For example, in an area in which one or more items are stored and no biological activity is anticipated and/or desired, ultraviolet source component 12 can generate ultraviolet light that is shone within the area, and ultraviolet detector component 14 can detect the ultraviolet radiation within the area. Activity dynamics analyzer 20 can operate ultraviolet source component 12 to periodically shine ultraviolet light having substantially the same spectral power distribution, direction, intensity, etc. within the area. In this case, an amount of ultraviolet radiation detected by ultraviolet detector component 14 each time the ultraviolet radiation is shone should not change significantly over time (absent any relocation, removal, addition, etc., of items in the area). To this extent, a significant change in the amount of ultraviolet radiation detected by ultraviolet detector component 14 can indicate the presence of biological activity. For example, in an embodiment, a one percent change in the amount of ultraviolet radiation detected comprises a significant change that indicates the presence of biological activity.

An embodiment of the invention includes an activity dynamics analyzer 20 configured to determine the set of biological activity dynamics and identify when a population, such as a bacteria population, is undergoing exponential growth based on the sensed ultraviolet radiation. When an organism, such as bacteria is entering the exponential growth phase, the population growth is accompanied by a spontaneous rapid change in the luminescence under ultraviolet light. In this case, activity dynamics analyzer 20 can periodically evaluate the ultraviolet luminescence of an area to determine whether a bacteria population is undergoing exponential growth. In addition to the rapid change in the ultraviolet luminescence, activity dynamics analyzer 20 can analyze an intensity and spectral content of the luminescence to determine a type of the organism, e.g., by direct comparison with tabulated responses of known bacteria types. Activity dynamics analyzer 20 also can utilize an amount of time since an exponential growth phase was detected to evaluate a potential for poison accumulation in an area (e.g., on a stored item). The period between each evaluation can be selected using any solution. For example, the period can be selected so that multiple evaluations are performed during a time period for the exponential growth phase of the organism. To this extent, for a twenty minute exponential growth period, the evaluations can be periodically performed approximately every thirty seconds. In this manner, activity dynamics analyzer 20 can ensure detection of the exponential growth period relatively early in the phase.

Further, absorption of a sufficient amount of ultraviolet radiation by a DNA molecule 2 destroys the DNA molecule 2, which can prevent the reproduction process of the corresponding organism, e.g., bacteria. To this extent, in response to an indication of the presence of biological activity, activity dynamics analyzer 20 can operate ultraviolet source component 12 to generate a suppressing dose of ultraviolet radiation of a sufficient amount and type of ultraviolet radiation to harm the DNA 2 of a target organism, such as bacteria. In this manner, ultraviolet source component 12 also can be used to suppress an amount of organism activity. For example, experimental results using *Escherichia coli* (ATCC 11303) bacteria obtained from American Type Culture Collection, yielded a six Log reduction (99.9999%) of bacteria concentration with a dose of approximately nine Millijoules per milliliter (mJ/ml) of 275-280 nanometer ultraviolet radiation. In an embodiment, ultraviolet source component 12 includes a set of ultraviolet radiation emitters 16 that are capable of generating the higher dose of ultraviolet radiation and are only utilized by activity dynamics analyzer 20 to suppress biological activity.

In the experiment, after activation and incubation, the bacteria suspension was diluted into different concentrations with phosphate-buffered saline (PBS) Buffer or sterile water and subjected to UV light exposure. After irradiation with a deep ultraviolet (DUV) LED and incubation for 18-22 hours, the enumeration of the bacteria as colony forming units (CFUs) was done using the Colilert-18 method. Reduction of bacteria concentration in water was expressed as $\log(N_b/N_a)$, where $N_b$ and $N_a$ are the concentrations of viable organisms before and after irradiation, respectively. For the germicidal experiments, LED devices were submerged into water (sample of 200 ml or more) and, therefore, the UV dosage normalized to the volume of water was calculated. The maximum germicidal efficiency was obtained for LEDs emitting at 275-280 nm, which is associated with the optimum combination of transmittance spectrum of water and absorption spectra of DNA and proteins. Log reduction of bacteria concentration varied linearly with the UV dosage, with the six Log reduction (99.9999%) obtained at dose of nine mJ/ml. Further, bacteria inactivation in a flowing water reactor was demonstrated using a 280 nanometer deep ultraviolet LED. A reduction of 96.3% was obtained for a water flow rate of approximately 0.1 gallons per minute (GPM) with an input power consumption of only 2.4 Watts.

The expected effect of ultraviolet radiation exposure is in defecting the bacteria's DNA, which prevents it from replicating. In an embodiment, an amount of the suppressing exposure generated by ultraviolet radiation source 12 is configured to be sufficient to return the bacteria population to a level of or lower than a population level that preceded an exponential growth phase. Further, activity dynamics analyzer 20 can enable a user to determine/select an amount of ultraviolet radiation exposure (e.g., intensity and time) used to harm an organism. Still further, after applying the ultraviolet radiation exposure, activity dynamics analyzer 20 can analyze an effectiveness of the suppression dose. For example, activity dynamics analyzer 20 can determine whether the ultraviolet absorption level for the area was successfully returned to a level of ultraviolet absorption that is at or below the level before the bacteria entered the exponential growth phase. A return to such a level of ultraviolet absorption can indicate that the bacteria population has returned to a level of or lower than the population level that preceded the exponential growth phase. Activity dynamics analyzer 20 can adjust one or more aspects of the suppression dose (e.g., time and/or intensity) in response to the effectiveness of the previous suppression dose. Still further, activity dynamics analyzer 20 can reapply a suppressing dose of ultraviolet radiation when the previous suppressing dose is evaluated as being insufficient.

Figure 2:
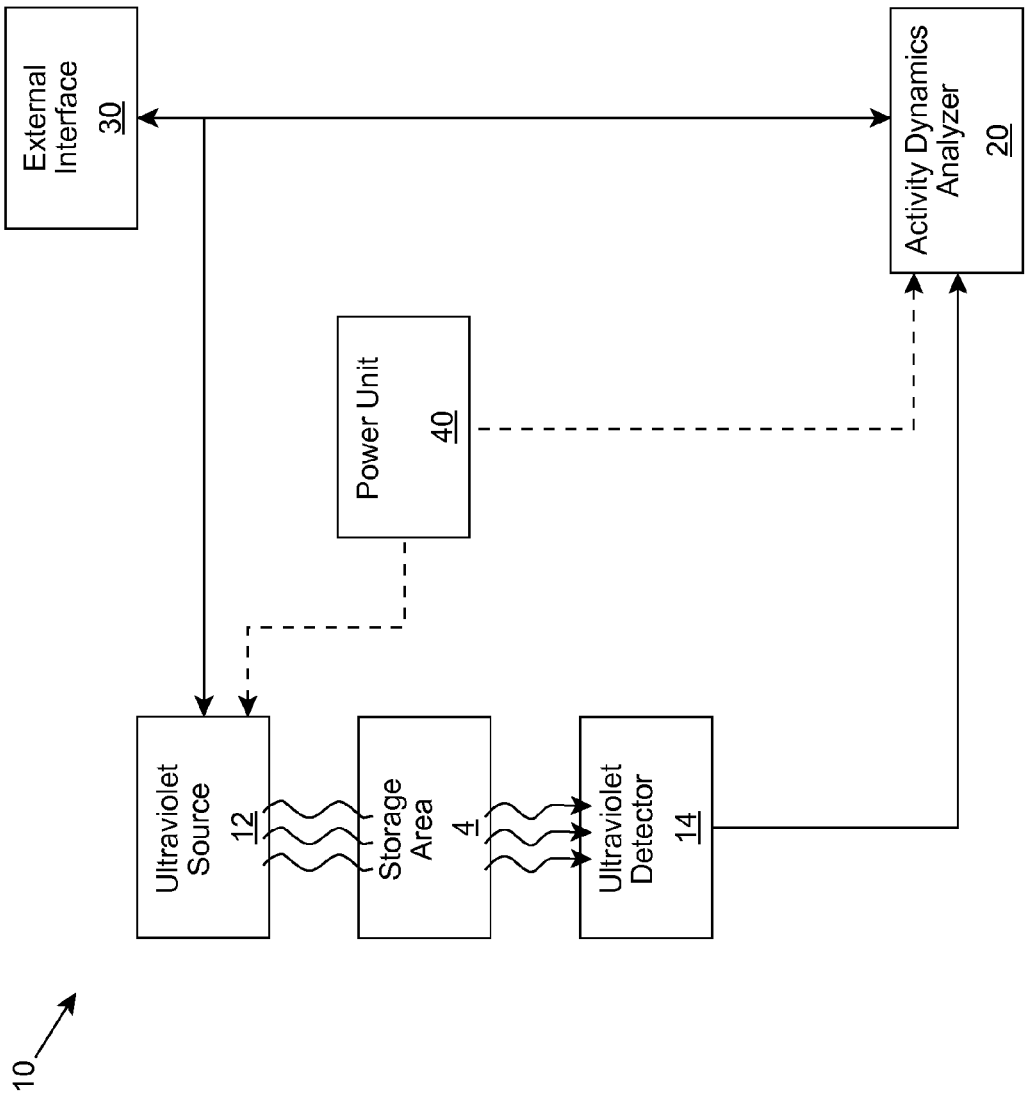
FIG. 2 shows an illustrative implementation of the system of FIG. 1 according to an embodiment.

FIG. 2 shows an illustrative implementation of system 10 according to an embodiment. In this implementation, system 10 is configured to monitor a set of biological activity dynamics in a storage area 4. Storage area 4 can be configured to store any type of one or more items within an area that is capable of being enclosed/sealed. For example, storage area 4 can comprise a portable storage device, such as a cooler, which can be utilized for storing food, medical equipment, and/or the like.

System 10 includes an activity dynamics analyzer 20, which is configured to operate ultraviolet source component 12 and analyze the ultraviolet light detected by ultraviolet detector component 14 over time to monitor biological activity within the storage area 4. In particular, activity dynamics analyzer 20 can control the location, direction, pattern, duration, intensity, wavelength, and/or the like, of the ultraviolet radiation that is generated by a set of emitters in ultraviolet source component 12 and shone within storage area 4. Further, activity dynamics analyzer 20 can control the location, direction, sensitivity, and/or the like of a set of detectors in ultraviolet detector component 14 and receive signal(s) from ultraviolet detector component 14 representative of the detected ultraviolet radiation. Activity dynamics analyzer 20 can process the detected ultraviolet radiation relative to the ultraviolet radiation that was shone within storage area 4 to determine a set of biological activity dynamics for the storage area 4.

In an embodiment, activity dynamics analyzer 20 operates ultraviolet source component 12 in a manner that is configured to illuminate various areas (e.g., compartments, shelves, and/or the like) within storage area 4 with ultraviolet radiation. While monitoring the area, the level, direction, period, etc., of ultraviolet radiation illuminating the various areas within storage area 4 can be selected to minimize the exposure to ultraviolet radiation by the stored item(s). After an access event within storage area 4 (e.g., area is re-sealed/re-enclosed), activity dynamics analyzer 20 can operate in a calibration mode for a calibration period. In an embodiment, the calibration period is less than or equal to approximately thirty seconds. However, it is understood that any calibration period can be utilized. During calibration, activity dynamics analyzer 20 can operate ultraviolet source component 12 to emit ultraviolet radiation within the storage area 4, and receive data on the corresponding ultraviolet radiation sensed by ultraviolet detector component 14 for processing. Activity dynamics analyzer 20 can process the data on the detected ultraviolet radiation to create calibration data for the storage area 4.

Subsequently, activity dynamics analyzer 20 can operate in a monitoring mode, during which the calibration data is used to evaluate data corresponding to the ultraviolet radiation detected when substantially the same configuration of ultraviolet radiation is used to illuminate the storage area 4. Activity dynamics analyzer 20 can evaluate the data to determine whether a significant variation is present between the ultraviolet radiation detected during calibration versus that detected during monitoring. For example, a relatively rapid increase in the absorption of the ultraviolet radiation (e.g., indicated by a relatively rapid decrease in the amount of ultraviolet radiation detected by ultraviolet detector component 14) can indicate biological (bacterial) activity in the monitored area. In an embodiment, activity dynamics analyzer 20 evaluates an increase by a factor of three within approximately ten to twenty minutes as an indication of biological activity in the monitored area. However it is understood that the amount of time and increase can be adjusted based on the type(s) of organisms that are anticipated to be present and/or being monitored, and the corresponding growth attributes of the organisms. Activity dynamics analyzer 20 can store the results of the evaluation as activity data for the storage area 4.

Activity dynamics analyzer 20 can re-calibrate after each access event with respect to storage area 4. For example, each time storage area 4 is accessed (e.g., a door is opened) and subsequently re-sealed, activity dynamics analyzer 20 can re-calibrate. Further, activity dynamics analyzer 20 can turn off ultraviolet source component 12 when it detects that the storage area 4 is being accessed and only restart after storage area 4 has been re-sealed (e.g., after a period of time). Further, it is understood that storage area 4 can comprise multiple distinct sections/chambers that are individually monitored by activity dynamics analyzer 20. In this case, activity dynamics analyzer 20 can perform a re-calibration only upon a detection of a change in the stored item(s) within the particular section/chamber and/or access to the separate section/chamber within storage area 4.

Activity dynamics analyzer 20 can further operate an external interface component 30, which is configured to present various information for use by a user using any solution. External interface component 30 can include one or more components configured to present activity data in a visual manner, an audible manner, via electronic and/or telephonic communication solutions, and/or the like. The information presented can include an indication of an operating state of system 10 for use by a user. For example, illustrative operating states can include calibrating, monitoring, suppressing, and/or the like. Further, external interface component 30 can present information on a current evaluation of the set of biological activity dynamics within the storage area 4. For example, illustrative evaluations can include no detected biological activity, low level of biological activity, high amount of biological activity, and/or the like. Further, external interface component 30 can indicate a location of the biological activity (if any), an error indication for monitoring one or more portions of the area (e.g., a blocked or broken ultraviolet source or detector), one or more attributes of the environment within the area, and/or the like. Still further, external interface component 30 can enable a user to designate one or more attributes of the operation of activity dynamics analyzer 20 using any solution.

In an embodiment, system 10 includes a power unit 40 that is implemented separately from storage area 4 to supply power to one or more of the various components within system 10, such as ultraviolet source component 12 and activity dynamics analyzer 20. For example, storage area 4 may comprise a cooler or the like, which does not include or otherwise require any power source. Further, storage area 4 may comprise a power source that is insufficient to operate system 10 in addition to maintaining one or more aspects of the environment within storage area 4 for a desired period of time. Regardless, power unit 40 can be utilized to operate system 10. Power unit 40 can comprise any source of power including, but not limited to, a battery set, an automotive charger, a solar cell, and/or the like. In an embodiment, activity dynamics analyzer 20 can implement multiple modes of operation depending on the source of power. In particular, when a power unit 40 of limited capacity is being utilized, one or more functions of system 10 can be disabled and/or reduced to lengthen an operating time for system 10. For example, use of ultraviolet source component 12 to suppress the biological activity by generating a higher intensity of ultraviolet radiation can be disabled.

Figure 3:
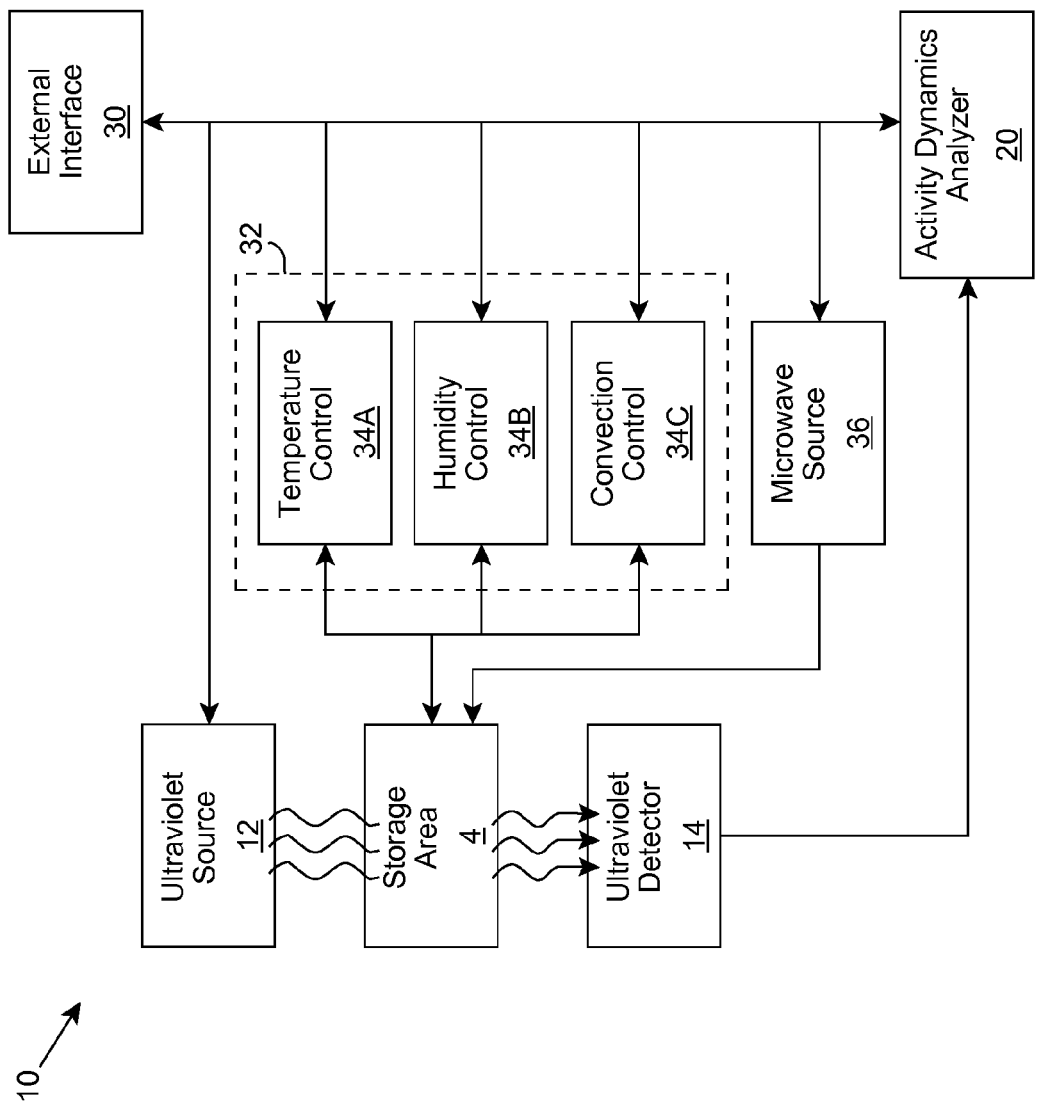
FIG. 3 shows another illustrative implementation of the system of FIG. 1 according to an embodiment.

FIG. 3 shows another illustrative implementation of system 10 according to an embodiment. In this implementation, system 10 is configured to monitor a set of biological (e.g., bacterial) activity dynamics in an environmentally controlled storage area 4. Storage area 4 can be configured to store any type of one or more items. For example, storage area 4 can comprise a temperature and/or humidity controlled area for storing food, medical equipment, and/or the like. In an embodiment, storage area 4 comprises the storage area of a refrigeration device, which is configured to store one or more refrigerated items.

As discussed herein, activity dynamics analyzer 20 can operate ultraviolet source component 12 to generate and shine ultraviolet radiation within area(s) of storage area 4 and monitor the ultraviolet radiation sensed by ultraviolet detector component 14 within storage area 4. Activity dynamics analyzer 20 can process the detected ultraviolet radiation to determine a set of biological activity dynamics. For example, activity dynamics analyzer 20 can monitor the detected ultraviolet radiation for a calibration time period to generate calibration data for the storage area 4. The activity dynamics analyzer 20 can subsequently compare differences in the detected ultraviolet radiation over a period of time with the calibration data to determine the set of biological activity dynamics. Activity dynamics analyzer 20 can operate an external interface component 30 to present various information on the operation of system 10 and/or the biological activity within storage area 4 for use by a user.

An environment within storage area 4 is controlled by an environmental control component 32. In an illustrative implementation, environmental control component 32 can comprise a temperature control module 34A, a humidity control module 34B, and a convection control module 34C. During normal operation of environmental control component 32, a user (e.g., using external interface component 30) can select a desired temperature, humidity, and/or the like to maintain within storage area 4. Environmental control component 32 can subsequently operate one or more cooling/heating components of temperature control module 34A to maintain the desired temperature, operate one or more humidifying/dehumidifying components of humidity control module 34B to maintain the desired humidity, operate one or more air or fluid convection components (e.g., fan, pump, vent, valve, etc.) of convection control module 34C to assist in maintaining a relatively even temperature/humidity within storage area 4, and/or the like.

In addition to monitoring biological activity within storage area 4, activity dynamics analyzer 20 can be configured to suppress biological activity that is determined to be occurring within storage area 4. For example, activity dynamics analyzer 20 can increase a duration, intensity, and/or the like, of ultraviolet radiation that ultraviolet source component 12 shines within a particular region of storage area 4 within which activity dynamics analyzer 20 has determined that biological activity is occurring. Further, activity dynamics analyzer 20 can adjust a direction of the ultraviolet radiation shone within the region of storage area 4 to increase the absorption by the target organism (e.g., bacteria).

Additionally, activity dynamics analyzer 20 can operate a microwave source component 36 in response to a determination of biological activity occurring within storage area 4. Microwave source component 36 can include one or more components for emitting microwave radiation within storage area 4. For example, microwave source component 36 can include one or more microwave emitters that are configured to generate and emit a focused beam of microwave radiation. Microwave source component 36 also can include one or more components for relocating and/or redirecting the microwave emitter(s) within storage area 4. Activity dynamics analyzer 20 can operate microwave source component 36 to emit microwave radiation directed to a section of storage area 4 within which biological activity has been determined to be occurring. Microwave source component 35 can emit the microwave radiation for a sufficient time and intensity to harm the target organism and thereby suppress the biological activity. In an embodiment, a time duration and intensity of the microwave exposure is selected such that an average temperature of the exposed item(s) and an average ambient temperature in the monitored area do not increase more than a few degrees centigrade. After emitting the microwave radiation, activity dynamics analyzer 20 can evaluate an effectiveness of the microwave radiation based on ultraviolet radiation that is subsequently detected by ultraviolet detector 14 and adjust the operation of microwave source 36 based on the evaluation using any solution.

Activity dynamics analyzer 20 also can adjust the operation of environmental control component 32 in response to a determination of biological activity occurring within storage area 4. For example, activity dynamics analyzer 20 can adjust a target temperature for the interior of storage area 4 to a temperature that is less conducive to the determined biological activity. In response, temperature control module 34A can adjust the temperature within storage area 4 accordingly. Further, activity dynamics analyzer 20 can adjust a target humidity for the interior of storage area 4 to a humidity that is less conducive to the determined biological activity. In response, humidity control module 34B can adjust the humidity level within storage area 4 accordingly. Still further, activity dynamics analyzer 20 can adjust the desired air/fluid flow through storage area 4 to isolate a section within storage area 4 within which biological activity has been determined to be occurring from the remainder of storage area 4 in order to limit the spread of the biological activity to other sections within storage area 4. In response, convection control module 34C can operate one or more components to partially or completely block/halt the air/fluid convection through the designated section of storage area 4.

It is understood that while various approaches for suppressing biological activity have been shown and described, activity dynamics analyzer 20 can implement any one or any combination of two or more of the approaches to suppress the biological activity. For example, activity dynamics analyzer 20 can operate ultraviolet source component 12 and/or microwave source component 36 to directly harm a target organism and subsequently operate environmental control component 32 to suppress an ability of the target organism to recover and/or spread within storage area 4. Further, activity dynamics analyzer 20 can implement multiple modes of operation for monitoring and/or suppressing biological activity, which can be selected by a user via external interface 30 and/or selected by activity dynamics analyzer 20 based on power requirements or the like. For example, illustrative modes of operation can include, but are not limited to: detection only, in which no suppression operations are performed; UV treatment only, in which only ultraviolet radiation is used to suppress biological activity; auto spoilage prevention/maximum storage time, in which activity dynamics analyzer 20 can utilize any combination of suppression approaches to suppress biological activity (and therefore delay spoilage) for the longest period of time; temperature adjustment only, in which only temperature is used to suppress biological activity; and/or the like.

Figure 4:
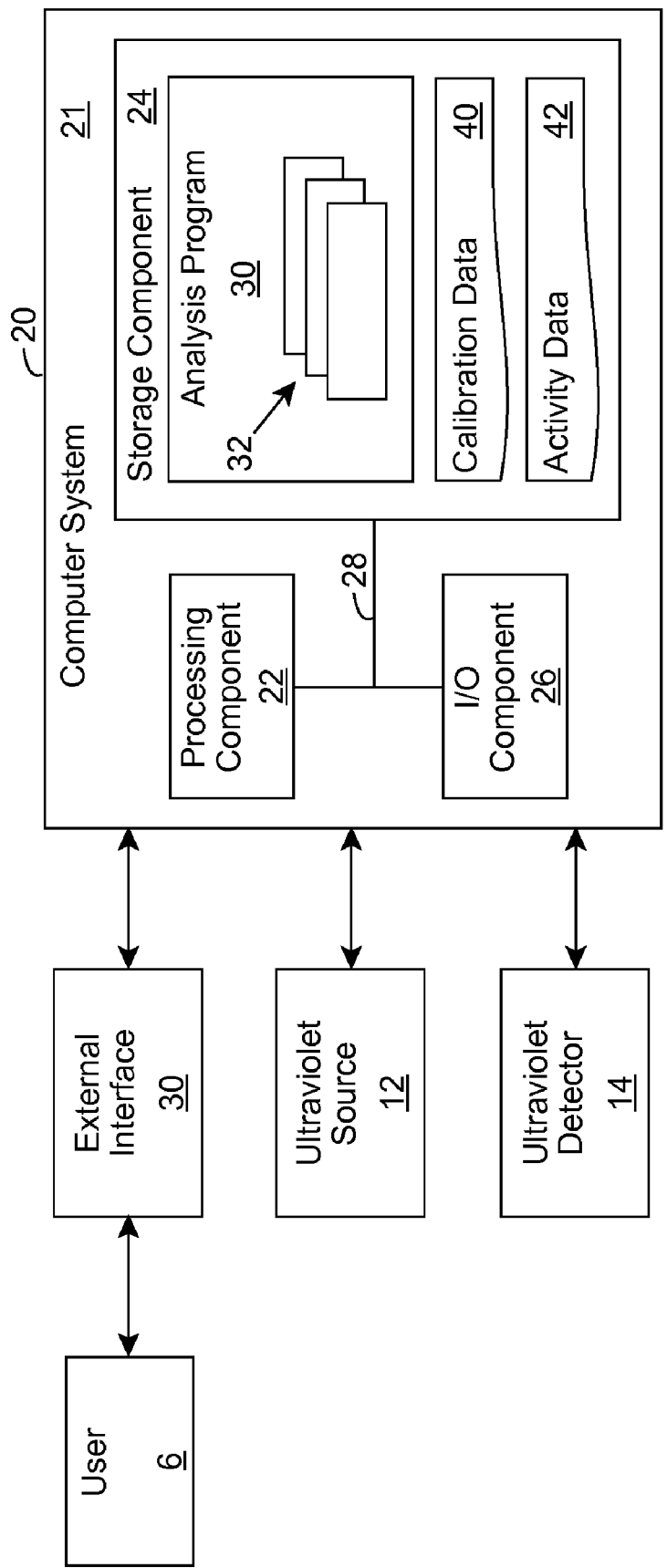
FIG. 4 shows an illustrative implementation of the activity dynamics analyzer of FIGS. 2 and 3 according to an embodiment.

FIG. 4 shows an illustrative implementation of activity dynamics analyzer 20 according to an embodiment. In this case, activity dynamics analyzer 20 is implemented as a computer system 21 including an analysis program 30, which makes computer system 21 operable to monitor and/or suppress biological activity within an area by performing a process described herein. In particular, analysis program 30 can operate ultraviolet source component 12 to shine ultraviolet radiation within an area and process data representing ultraviolet radiation detected within the area by ultraviolet detector component 14. During an initial period of operation (e.g., after recent access to the area, addition/removal/reconfiguration of item(s) placed within the area, and/or the like), analysis program 30 can generate calibration data 40 based on the detected ultraviolet radiation. After a calibration period, analysis program 30 can process data representing the detected ultraviolet radiation to generate activity data 42 for the area. The activity data 42 can include information on the location, type, severity, phase, and/or the like, of biological activity, if any, that is occurring within the monitored area. Analysis program 30 can use activity data 42 to suppress the biological activity and/or provide the activity data 42 for use by user 6 as discussed herein.

Computer system 21 is shown including a processing component 22 (e.g., one or more processors), a storage component 24 (e.g., a storage hierarchy), an input/output (I/O) component 26 (e.g., one or more I/O interfaces and/or devices), and a communications pathway 28. In general, processing component 22 executes program code, such as analysis program 30, which is at least partially fixed in storage component 24. While executing program code, processing component 22 can process data, which can result in reading and/or writing transformed data from/to storage component 24 and/or I/O component 26 for further processing. Pathway 28 provides a communications link between each of the components in computer system 20. I/O component 26 and/or external interface component 30 can comprise one or more human I/O devices, which enable a human user 6 to interact with computer system 21 and/or one or more communications devices to enable a system user 6 to communicate with computer system 21 using any type of communications link. To this extent, analysis program 30 can manage a set of interfaces (e.g., graphical user interface(s), application program interface, and/or the like) that enable human and/or system users 6 to interact with analysis program 30. Further, analysis program 30 can manage (e.g., store, retrieve, create, manipulate, organize, present, etc.) the data, such as calibration data 40 and activity data 42, using any solution.

In any event, computer system 21 can comprise one or more general purpose computing articles of manufacture (e.g., computing devices) capable of executing program code, such as analysis program 30, installed thereon. As used herein, it is understood that "program code" means any collection of instructions, in any language, code or notation, that cause a computing device having an information processing capability to perform a particular function either directly or after any combination of the following: (a) conversion to another language, code or notation; (b) reproduction in a different material form; and/or (c) decompression. To this extent, analysis program 30 can be embodied as any combination of system software and/or application software.

Further, analysis program 30 can be implemented using a set of modules 32. In this case, a module 32 can enable computer system 21 to perform a set of tasks used by analysis program 30, and can be separately developed and/or implemented apart from other portions of analysis program 30. When computer system 21 comprises multiple computing devices, each computing device can have only a portion of analysis program 30 fixed thereon (e.g., one or more modules 32). However, it is understood that computer system 21 and analysis program 30 are only representative of various possible equivalent computer systems that may perform a process described herein. To this extent, in other embodiments, the functionality provided by computer system 21 and analysis program 30 can be at least partially implemented by one or more computing devices that include any combination of general and/or specific purpose hardware with or without program code. In each embodiment, the hardware and program code, if included, can be created using standard engineering and programming techniques, respectively.

Regardless, when computer system 21 includes multiple computing devices, the computing devices can communicate over any type of communications link. Further, while performing a process described herein, computer system 21 can communicate with one or more other computer systems, such as user 6, using any type of communications link. In either case, the communications link can comprise any combination of various types of wired and/or wireless links; comprise any combination of one or more types of networks; and/or utilize any combination of various types of transmission techniques and protocols.

In addition to the use of ultraviolet radiation to monitor an area for biological activity, an embodiment of system 10 generates and emits visible light (e.g., radiation having a wavelength between approximately 400 nanometers and approximately 600 nanometers) within an area and acquires data on the monitored area for use in identifying the biological activity. To this extent, ultraviolet source 12 can include one or more narrow and/or broad band visible light emitters, such as light emitting diodes. In this case, activity dynamics analyzer 20 can process the visible light-based data to determine whether any change occurred to the item(s) within an area after the area is subsequently re-sealed (e.g., to determine whether re-calibration is necessary). Further, activity dynamics analyzer 20 can process the visible light-based data to determine one or more aspects of the biological activity dynamics (e.g., type of bacteria). More sophisticated processing of the visible light-based data can be performed to obtain spatial images and mapping of the contamination and/or purification process in space and time, which system 10 can use to improve/optimize a spatial distribution of a suppressing exposure (e.g., ultraviolet, microwave, or the like).

Returning to FIG. 1, system 10 can be implemented within an existing storage device (e.g., a refrigerator) using any solution. For example, one or more emitters 16 and detectors 18 can be fixed within various locations in the storage device (e.g., on walls, shelves, etc.) and configured for operation by an activity dynamics analyzer 20. The locations of emitters 16 and detectors 18 can be selected to provide comprehensive coverage of the storage area even with the presence of one or more stored items. Activity dynamics analyzer 20 can be located outside of the storage area of the storage device. Alternatively, system 10 can be integrated into a new storage device while the storage device is being built using any solution.

The foregoing description of various aspects of the invention has been presented for purposes of illustration and description. It is not intended to be exhaustive or to limit the invention to the precise form disclosed, and obviously, many modifications and variations are possible. Such modifications and variations that may be apparent to an individual in the art are included within the scope of the invention as defined by the accompanying claims.

What is claimed is:

1. A system comprising:
an ultraviolet radiation source configured to generate ultraviolet radiation shone within an area;
an ultraviolet radiation detector configured to sense ultraviolet radiation within the area; and
a computer system including at least one computing device, wherein the computer system is configured to:
monitor the ultraviolet radiation sensed by the ultraviolet radiation detector over a period of time;
determine a set of biological activity dynamics for the area based on the sensed ultraviolet radiation and the period of time, wherein the set of biological activity dynamics includes: a current growth phase of an organism within the area and an estimated amount of time the organism has been in the growth phase; and
control the ultraviolet radiation generated by the ultraviolet radiation source by adjusting at least one of: a direction, an intensity, a pattern, or a spectral power of the ultraviolet radiation in response to the set of biological activity dynamics.

2. The system of claim 1, wherein the computer system is further configured to adjust at least one environmental condition of the area in response to the set of biological activity dynamics.

3. The system of claim 2, wherein the at least one environmental condition includes at least one of: a temperature, a humidity, a gas convection, or a fluid convection.

4. The system of claim 1, further comprising a refrigeration device, wherein the area is a storage area of the refrigeration device.

5. The system of claim 1, wherein the computer system is further configured to present an indication of at least one of: an operating state of the ultraviolet radiation source or the set of biological activity dynamics for use by a user.

6. A system comprising:
an ultraviolet radiation source configured to generate ultraviolet radiation shone within an area;
an ultraviolet radiation detector configured to sense ultraviolet radiation within the area; and
a computer system including at least one computing device, wherein the computer system is configured to:
monitor the ultraviolet radiation sensed by the ultraviolet radiation detector over a period of time;
determine a set of biological activity dynamics for the area based on the sensed ultraviolet radiation and the period of time, wherein the set of biological activity dynamics includes: a current growth phase of an organism within the area and an estimated amount of time the organism has been in the growth phase; and
suppress biological activity in the area in response to the set of biological activity dynamics.

7. The system of claim 6, wherein the computer system operates a microwave radiation source configured to emit microwave radiation within the area to suppress the biological activity.

8. The system of claim 6, wherein the computer system operates a second ultraviolet radiation source configured to emit a higher intensity of ultraviolet radiation than the ultraviolet radiation source to suppress the biological activity.

9. The system of claim 6, further comprising a refrigeration device, wherein the area is a storage area of the refrigeration device.

10. A storage device comprising:
a storage area configured to store at least one item;
an ultraviolet radiation source configured to generate ultraviolet radiation shone within the storage area;
an ultraviolet radiation detector configured to sense ultraviolet radiation within the storage area; and
a computer system including at least one computing device, wherein the computer system is configured to:
monitor the ultraviolet radiation sensed by the ultraviolet radiation detector over a period of time;
determine a set of biological activity dynamics for the storage area based on the monitored ultraviolet radiation and the period of time, wherein the set of biological activity dynamics includes: a current growth phase of an organism within the area and an estimated amount of time the organism has been in the growth phase; and
control the ultraviolet radiation generated by the ultraviolet radiation source by adjusting at least one of: a direction, an intensity, a pattern, or a spectral power of the ultraviolet radiation in response to the set of biological activity dynamics.

11. The device of claim 10, wherein the computer system is further configured to present an indication of at least one of: an operating state of the ultraviolet radiation source or the set of biological activity dynamics for use by a user.

12. The device of claim 10, wherein the computer system is further configured to control at least one environmental condition of the storage area, wherein the at least one environmental condition includes at least one of: a temperature, a humidity, a gas convection, or a fluid convection.

13. A storage device comprising:
a storage area configured to store at least one item;
an ultraviolet radiation source configured to generate ultraviolet radiation shone within the storage area;
an ultraviolet radiation detector configured to sense ultraviolet radiation within the storage area; and
a computer system including at least one computing device, wherein the computer system is configured to:
monitor the ultraviolet radiation sensed by the ultraviolet radiation detector over a period of time;
determine a set of biological activity dynamics for the storage area based on the monitored ultraviolet radiation and the period of time, wherein the set of biological activity dynamics includes: a current growth phase of an organism within the area and an estimated amount of time the organism has been in the growth phase; and
suppress biological activity in the storage area in response to the set of biological activity dynamics.

14. The device of claim 13, wherein the computer system suppresses the biological activity by controlling at least one of: at least one environmental condition of the storage area, a microwave radiation source, or a second ultraviolet radiation source.

15. The device of claim 13, wherein the computer system suppresses the biological activity using a plurality of operating modes, wherein a user can select a desired operating mode for use in suppressing the biological activity.

16. A refrigeration device comprising:
a storage area configured to store at least one refrigerated item;
an ultraviolet radiation source configured to generate ultraviolet radiation shone within the storage area;
an ultraviolet radiation detector configured to sense ultraviolet radiation within the storage area; and a computer system including at least one computing device, wherein the computer system is configured to control at least one environmental condition of the storage area, wherein the at least one environmental condition includes at least one of: a temperature, a humidity, a gas convection, or a fluid convection, and wherein the computer system is configured to monitor the ultraviolet radiation sensed by the ultraviolet radiation detector over a period of time and to determine a set of biological activity dynamics for the storage area based on the monitored ultraviolet radiation and the period of time, wherein the set of biological activity dynamics includes: a current growth phase of an organism within the area and an estimated amount of time the organism has been in the growth phase.

17. The device of claim 16, wherein the computer system is further configured to suppress biological activity in the storage area in response to the set of biological activity dynamics.

18. The device of claim 16, wherein the computer system is further configured to control the ultraviolet radiation generated by the ultraviolet radiation source, wherein the computer system controls the ultraviolet radiation by adjusting at least one of: a direction, an intensity, a pattern, or a spectral power of the ultraviolet radiation.

19. The device of claim 16, wherein the computer system is further configured to detect an access event within the storage area, wherein the computer system monitors the ultraviolet radiation in a calibration mode for a calibration period in response to the access event, and wherein the calibration mode re-calibrates a baseline used to determine the set of biological activity dynamics for the area.

20. A storage device comprising:
a storage area configured to store at least one item;
an ultraviolet radiation source configured to generate ultraviolet radiation shone within the storage area;
an ultraviolet radiation detector configured to sense ultraviolet radiation within the storage area; and
a computer system including at least one computing device, wherein the computer system is configured to:
monitor the ultraviolet radiation sensed by the ultraviolet radiation detector over a period of time;
determine a set of biological activity dynamics for the storage area based on the monitored ultraviolet radiation and the period of time, wherein the set of biological activity dynamics includes: a current growth phase of an organism within the area and an estimated amount of time the organism has been in the growth phase; and
detect an access event within the storage area, wherein the computer system monitors the ultraviolet radiation in a calibration mode for a calibration period in response to the access event, and wherein the calibration mode re-calibrates a baseline used to determine the set of biological activity dynamics for the area.

21. The storage device of claim 20, wherein the computer system is further configured to control the ultraviolet radiation generated by the ultraviolet radiation source by adjusting at least one of: a direction, an intensity, a pattern, or a spectral power of the ultraviolet radiation in response to the set of biological activity dynamics.

* * * * *